United States Patent [19]

Kacerek

[11] 4,157,499
[45] Jun. 5, 1979

[54] BLOOD CELL COUNTER HAVING DUAL TESTING HEADS

[75] Inventor: John Kacerek, West Caldwell, N.J.

[73] Assignee: Becton, Dickinson and Company, East Rutherford, N.J.

[21] Appl. No.: 833,560

[22] Filed: Sep. 15, 1977

[51] Int. Cl.² .............................................. G01N 27/00
[52] U.S. Cl. ............................. 324/71 CP; 204/195 R
[58] Field of Search .................... 324/71 CP, 71 R; 235/92 PC; 204/195 R

[56] References Cited

U.S. PATENT DOCUMENTS

| 3,793,587 | 2/1974 | Thom | 324/71 CP |
| 3,997,838 | 12/1976 | Shamos et al. | 324/71 CP |
| 4,076,419 | 2/1978 | Kleker | 324/71 CP |

Primary Examiner—M. Tokar
Attorney, Agent, or Firm—Kane, Dalsimer, Kane, Sullivan and Kurucz

[57] ABSTRACT

A hematology analyzer for counting red blood cells and white blood cells wherein separate counting heads and circuits are provided for counting each type of blood cell. Tests may be run separately or simultaneously during the counting operation. The operation of each head is optimized, thereby yielding greater reliability, precision, accuracy, speed, and efficiency. Electronic circuitry generates pulses as each cell passes through a sensing zone. A real time display of these pulses is provided on a cathode ray tube display.

16 Claims, 3 Drawing Figures

BLOOD CELL COUNTER HAVING DUAL TESTING HEADS

BACKGROUND OF THE INVENTION

The field of the invention involves particle counters for analyzing blood cells and platelets suspended in liquid media.

Three methods presently exist for the counting of blood cells. These include: (1) manually counting the cells in a known dilution by use of a microscope; (2) semi-automated systems, in which proper dilutions are first prepared independently, and the dilutions are then introduced to an instrument for electronic cell counting; (3) fully automated systems wherein the blood sample is directly introduced into an instrument which performs all required functions, including dilutions and counts. The first has the disadvantage of being slow, laborious, and subject to human error in counting. The third had the disadvantage of being very expensive.

Automatic and semi-automatic hematology analyzers currently in use electronically count blood cells by use of detectors which detect the difference in conductivity between the cells and the diluent. Such analyzers take advantage of the fact that blood cells are relatively poor conductors whereas the diluent is a relatively good electrical conductor.

In operation, a sample is drawn through a filter and passes through an aperture in a typical blood cell counter. Electrodes are generally located above and below this aperture and serve to sense the changed resistance as a blood cell passes the electrode sensing area. The electrodes are connected to appropriate circuitry which generates a pulse in response to each cell passing through the aperture. The pulses are electronically totaled over a predetermined period, and the results generated, for example, on a calibrated meter as millions of red blood cells per cubic millimeter, or as thousands of white blood cells per cubic millimeter. Counting devices having the above features can be found in commonly assigned U.S. Pat. Nos. 3,783,376; 3,812,425; 3,861,800; and 3,973,194.

Because of the great differences in concentration between red blood cells and white blood cells (WBC) in blood, different dilutions are necessary to obtain accurate counts. In addition, a lysing agent must be added to the dilution to remove red blood cells when a WBC count is taken. Systems which utilize only one counting head therefore require a complete flushing of the instrument when, for example, an RBC is to be taken after a WBC assay. Even with flushing, the lysing agent often has a residual effect which can introduce inaccuracy in the RBC. Furthermore, two separate tests are required to determine RBC and WBC in systems having only one counting head, and such tests cannot be conducted simultaneously. Because of the disparity in size between WBC and RBC or platelets, it has also been advisable to change the aperture size between counts. These procedures are all time consuming for the operator.

Present systems which have the fluidics and circuitry to perform RBC and WBC simultaneously are fully automated systems, such as disclosed in U.S. Pat. No. 3,549,994. An inexpensive counter, capable of analyzing prediluted and/or lysed blood samples so as to simultaneously determine RBC and WBC, has not yet been developed.

SUMMARY OF THE INVENTION

In view of the above, it is the principal object of the present invention to provide an improved analyzer which overcomes the aforementioned shortcomings of the prior art analyzers. A specific object is to provide an analyzer capable of simultaneously conducting red and white blood cell counts or other quantitative hematology measurements. Another object is to provide a device which eliminates the need for thorough flush-out between red and white blood cell counts. Still another object is to provide a device which will save time and reduce the risk of cross-contamination between RBC and WBC dilutions. A further object is to provide an inexpensive, semi-automated analyzer which determines cell and platelet counts of pre-diluted samples.

Other objects and advantages of the invention will become apparent from the following description.

The above and other objects are attained in accordance with the present invention by providing a hematology analyzer which includes two separate counting heads. Each of the heads has separately sized aperture jewels, and the electronic circuitry associated with each head has both upper and lower threshold levels to distinguish noise signals from pulses created by the passage of a cell through the aperture. The analyzer is computer controlled to perform the following quantitative hematology measurements:
1. white blood cell count (WBC)
2. red blood cell count (RBC)
3. hemoglobin (Hb)
4. hematocrit (Hct)
5. mean corpuscular volume (MCV)
6. mean corpuscular hemoglobin (MCH)
7. mean corpuscular hemoglobin concentration (MCHC)
8. platelet blood count (PBC)

DESCRIPTION OF THE DRAWING

FIG. 3 shows a dual-type reservoir for containing diluted blood samples.

DETAILED DESCRIPTION OF THE INVENTION

Figure 1:
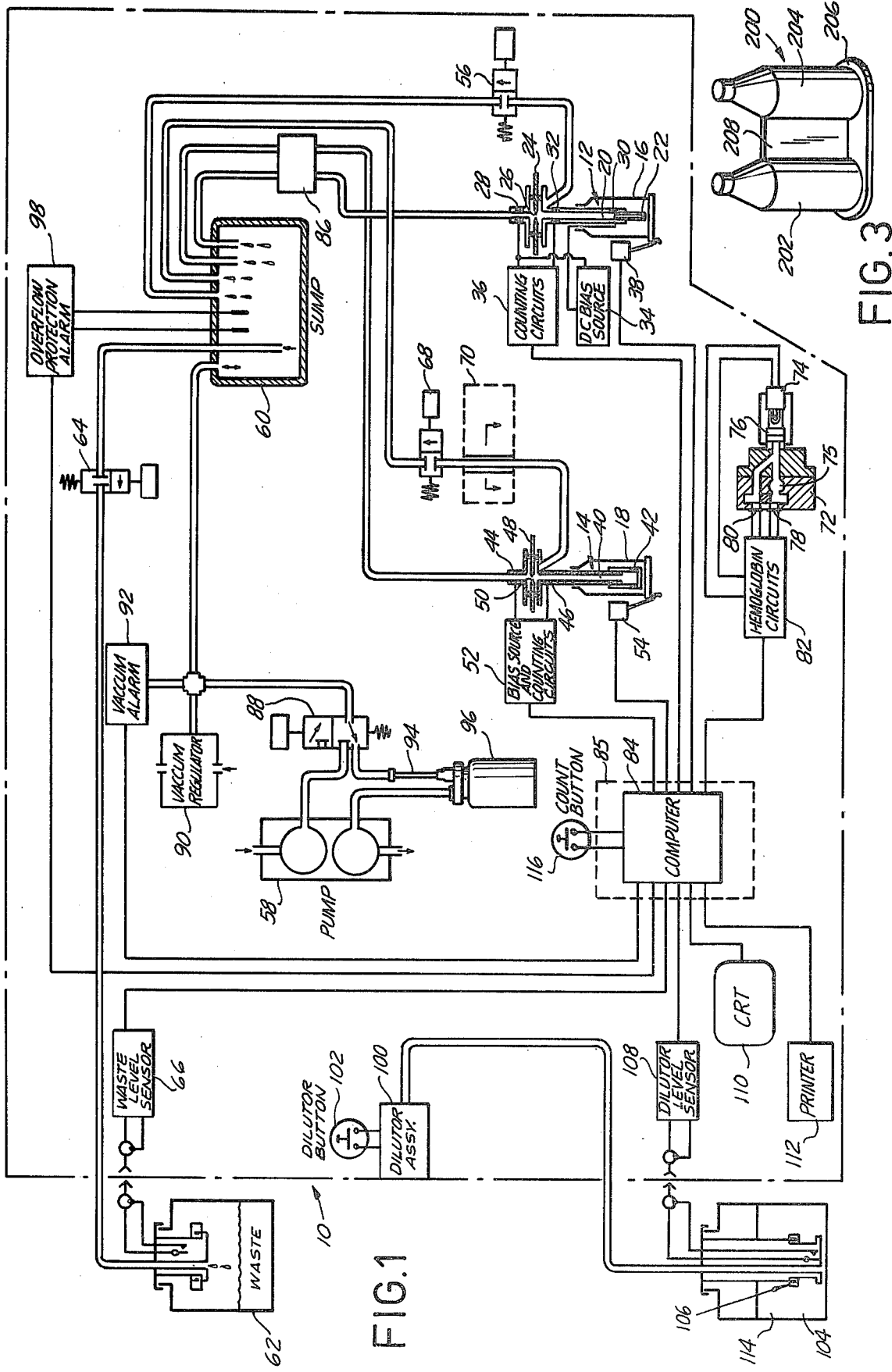
FIG. 1 is a schematic representation of the hematology analyzer of the present invention.

Reference is now made to the accompanying drawing wherein the present invention is depicted in the form of a blood analyzer.

In accordance with the present invention, the counter 10 includes two counting heads generally designated 12 and 14 respectively for measuring RBC and WBC. Reservoirs 16 and 18 in the form of containers are positioned such that portions of the heads 12 and 14 respectively, penetrate the diluted blood samples contained within them. That is, reservoir 16 contains a blood sample suitably diluted to permit RBC and reservoir 18 contains a blood sample suitably diluted and lysed to permit WBC.

The RBC head 12 includes an elongated sample tube 20 having a tube filter 22 positioned at its lower end extending into the reservoir. Provision is made for a jeweled aperture carrying slide 24 to be positioned within sample tube 20 proximal its upper end in a manner such that no leakage will occur. To this end, the mounting of the slide is substantially as shown in commonly assigned U.S. Pat. No. 3,783,376. The aperture 26 in slide 24 has a diameter of 70 microns.

Figure 2:
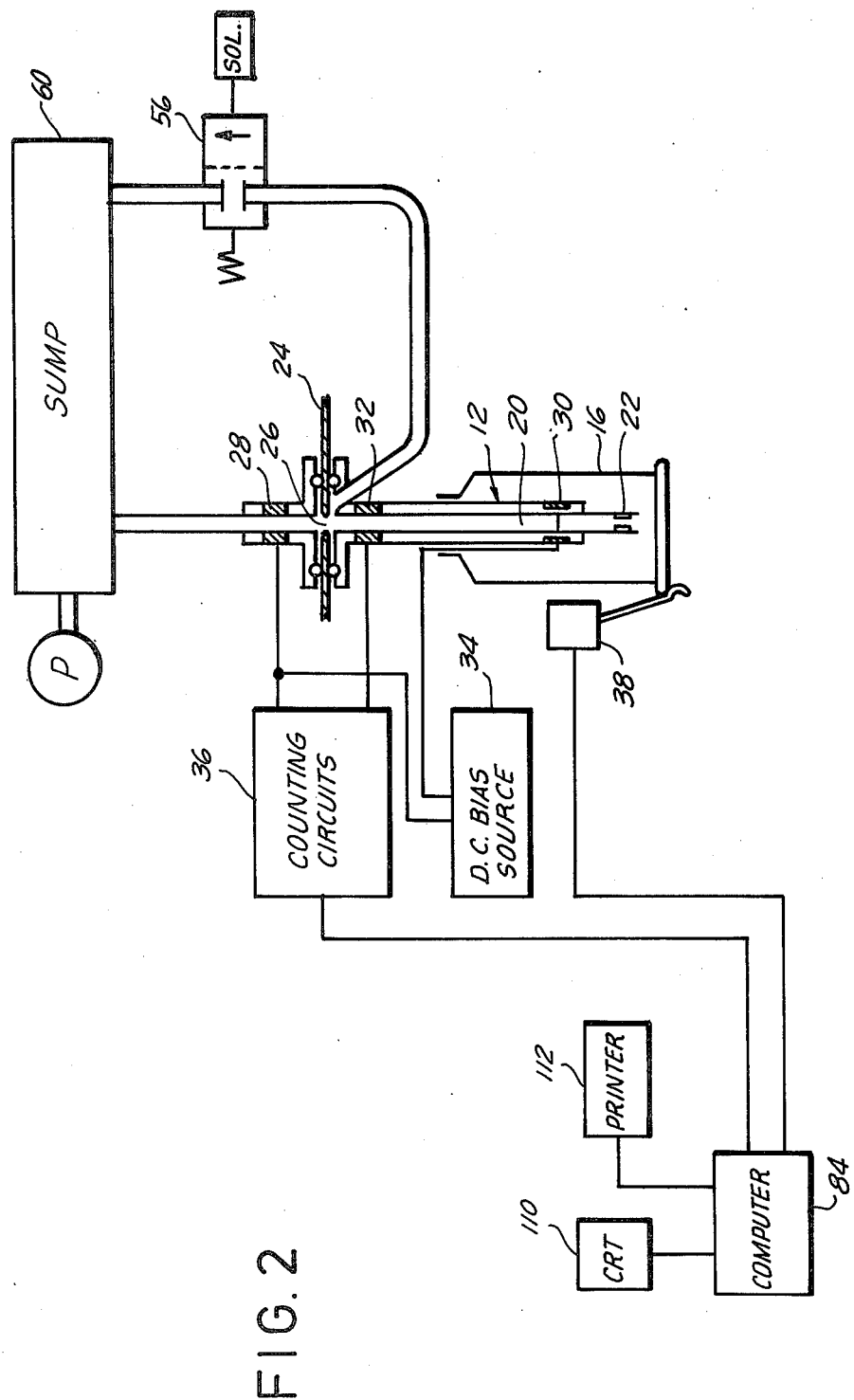
FIG. 2 is an enlargement of the RBC-PBC head.

The head further comprises a set of three electrodes 28, 30 and 32. A DC power source 34 is connected across electrodes 30 and 28, and the RBC/PBC transducing/counting circuitry 36 is connected across electrodes 32 and 28. A reservoir position switch 38 is also shown in FIG. 1. FIG. 2 illustrates these features with greater clarity. This head is described in detail in concurrently filed application "Particle Counter Having Three Electrode Head" by John Haynes, Ser. No. 833,559 filed Sept. 15, 1977.

The WBC head 14 comprises an elongated sample tube 40 having a filter 42 at its lower end extending into a reservoir 18. A pair of electrodes 44 and 46 are provided proximal the upper end of tube 40. As shown, the electrodes are spaced apart from each other and an aperture slide 48 carrying a jeweled aperture 50 is inserted between the electrodes. The mounting of slide 48 is similar to that for slides 24. Electrodes 44 and 46 are connected to an AC power source and counting may be accomplished by WBC counting circuits 52 in a conventional manner. The aperture 50 of the WBC head is 90 microns in diameter. A reservoir position switch 54 is also provided to make sure the reservoir is in place.

The RBC and WBC heads are both provided with flushing systems for clearing debris from the respective apertures. When valve 56 is actuated (through an associated solenoid), the vacuum created by pump 58 is purged causing the liquid in the sample tube 20 to flow at high velocity across the aperture slide to drain through valve 56 into sump 60. Periodically, the sump is pressurized by pump 58, thereby forcing liquid into waste container 62 through solenoid valve 64. A waste level sensor 66 is provided to insure that overflow of the waste container does not occur.

The WBC head purging system operates in substantially the same manner, and utilizes purge valve 68.

The hemoglobin head 70 is also located on the vacuum purge line of the WBC head between valve 68 and counting head 14. The hemoglobin head consists of a standard filter photometer and a micro-sample optical flow cell. Such heads, including their associated fiber optics block 72, lamp 74, 540 nm filter 76, sample and reference photosensors 78 and 80, and associated circuitry 82 are also utilized in analyzer Model HA-5, manufactured by the common assignee. Data processed by the hemoglobin circuits 82 is transmitted to microcomputer 84 as is data from both the RBC and WBC counting circuits.

The RBC and WBC heads are also in fluid communication with a dual pinch valve 86. This valve is closed during the purging operation, and open during the counting procedure.

The pump 58, which in this example is a dual electric diaphragm pump, can impart either positive or negative pressure on the sump 60. Three-way transfer valve 88, by means of a solenoid, determines the pressure which will be applied. A vacuum regulator 90 controls the amount of vacuum which is utilized, and a vacuum alarm 92 is provided to indicate when the vacuum is too low. Leaks within the system are thereby detected. The three-way valve also controls the flow through the restrictor assembly 94 and the accumulator 96 when negative pressure is applied to the sump 60. An overflow protection alarm 98 alerts the operator if the sump is in danger of overflowing, and stops the system at this point.

A built-in dilutor assembly 100 is provided within the counter 10, and will dispense a precise quantity of diluent to a sample upon actuation of dilutor button 102. A bulk reagent container 104 is provided for holding the diluent, and a magnetic float switch 106 and level sensor 108 insure that sufficient diluent is within the container. The level sensor is connected with computer 84, and provides the information to the computer to indicate when additional diluent must be added to the container.

The computer is connected to a cathode ray tube display 110 and a printer 112 which inform the operator of nearly all functions performed by the apparatus, including cell counts, dilution information, operating instructions, and warnings. The display also provides a real time pulse train together with indications of the upper and lower threshold limits. This feature is extremely advantageous for a number of reasons. If, for example, the operator observed mostly small pulses during a cell count, this could be indicative of a pathological condition. Large "blasts" can also be seen, such as those caused by large bubbles. The operator will then know, the instrument is malfunctioning. Instead of waiting for the machine to go through an entire counting cycle, which is about 40 seconds in this embodiment, the operator can quickly determine whether erroneous data is being generated. He can immediately purge the system or otherwise attempt to correct the malfunction, thereby saving the time necessary for the instrument to continue to count and calculate the erroneous results.

The operation of the hematology analyzer begins after the blood samples have been diluted at room temperature. Prediluted samples may be fed directly to the analyzer, or the built-in dilutor assembly 100 may be used. A primary dilution is made having a ratio of 260:1, and is used in determining WBC/Hb. A second dilution, using a sample from the first before addition of a lysing reagent containing a modified Drabkins Reagent, is made with a ratio of 260:1 for a resultant dilution of 67,600:1. This latter dilution is used for determining the RBC/Hct values.

When the dilutor assembly 100 indicates it is "READY TO ASPIRATE", button 102 is pushed and 35 microliters of whole blood specimen are aspirated from a specimen container (not shown) through a pipette (not shown). An indicator light (not shown) provides the above signal. After the blood has aspirated, another light will indicate that the dilutor is "READY TO DISPENSE". A mixture of the 35 microliters of blood and 9.1 ml of diluent will be dispensed when button 102 is again pushed. This provides the desired 260:1 dilution ratio.

To make an RBC/Hct dilution, 35 microliters of the 260:1 dilution are aspirated by the dilutor 100 and dispensed with 9.1 ml of diluent for a 67,600:1 dilution. The standard dilution ratios of 260:1 plus 3 to 4 drops of lysing and Hb reagent for the WBCHb WBC/Hb and 67,600:1 for the RBC/Hct head are permanently stored in the microcomputer.

Platelet counts are taken in the RBC head, but are done separately from the RBC procedure. Platelet-rich plasma is obtained by separating platelets from erythrocytes by sedimentation of whole blood. A 3.3 microliter sample of platelet-rich plasma is then added to 9.1 ml. of diluent to obtain a 2758:1 dilution.

The counting procedures begin after the analyzer 10 has been properly cleaned and calibrated. The purging system, which removes previous sample while simultaneously cleaning the aperture and hemoglobin head, is described in detail in a concurrently filed application entitled "Purging Means For Aperture of Blood Cell Counter", Ser. No. 852,953 filed Nov. 18, 1977. The counting circuits for both the RBC and WBC heads are substantially as described in commonly assigned U.S. Pat. No. 3,973,194, and include dual threshold levels to discriminate from noise caused by dirt, bubbles, or interference. Provision for dual threshold levels in a platelet counter is described in detail in copending application Ser. No. 738,896, entitled "Particle Density Measuring System", by John L. Haynes. A similar circuit may be employed within the present invention for utilization with cells as well as platelets.

The reservoirs 16 and 18 are positioned in a manner substantially as described in concurrently filed application by John Haynes entitled "Blood Cell Counter Having Three-Electrode Counting Head", Ser. No. 833,559 filed Sept. 15, 1977, and position switches 38 and 54 inform the computer that the reservoirs are in place. The count button 116 is then pushed, and the diluted samples are aspirated through apertures 26 and 50 in the respective heads. Pump 58 is responsible for generating the negative pressure within the system which is imparted to the counting head via sump 60.

As previously explained, the blood cells are far less conductive than the liquid medium in which they are suspended, and so cause a variation in the current flow between the sensing electrodes. Appropriate circuits 36 and 52 detect this variation, and produce a pulse as each cell flows through the aperture. Unlike the RBC head, the WBC sensing electrodes 44 and 46 are connected to an AC source. Bubble formation is minimized as the tendency to develop polarization potentials is eliminated. Commonly assigned U.S. Pat. No. 3,861,800 describes the AC head and associated circuitry in greater detail. The WBC counting circuit 52 operates in substantially the manner described in U.S. Pat. No. 3,973,194 to produce an analog signal representative of the number of white blood cells per unit volume. The computer receives the signal, and causes the count to be displayed on the printer and/or the cathode ray tube. The computer is also capable of statistically analyzing the counts received from the counting circuits, as described in concurrently filed patent application entitled "Method and Apparatus For Providing Accurate Blood Cell Counts", Ser. No. 833,558 filed Sept. 5, 1977 and now abandoned.

The RBC head operates in a similar manner, but utilizes a DC bias source 34 connected between electrodes 30 and 28. The detection circuitry is connected between electrodes 32 and 28. The advantages of such an arrangement is described in concurrently filed application "Blood Cell Counter Having Three-Electrode Head", by John Haynes. The counting circuits 36 are similar to those associated with the WBC head, and test results are displayed on printer 112 and/or cathode ray tube 110 by way of computer 84 which is within electronics package 85.

Platelet counting is also accomplished in the RBC head, but is not done simultaneously with the RBC. A separate dilution is prepared, and the counting process is identical to that described for the RBC. To obtain a quieter system while counting platelets or cells, restrictor 94 and accumulator 96 are employed. These act in conjunction with the sump 60 to provide a pneumatic filter assembly. Pressure pulses from the pump are reduced in this manner, and the accumulator also acts as a temporary waste receptacle.

Before the RBC and WBC have been determined, the heads are purged by means of solenoid controlled vacuum purge valves 56 and 58, respectively, and pump 58. Between valve 68 and head 14 is a hemoglobin (Hb) head 70. The hemoglobin head consists of a standard filter photometer and a micro-sample optical flow cell 75 and other components listed above. The Hb concentration is determined by measuring the light absorption of cyanmethemoglobin produced by the reaction of the diluted specimen with the modified Drabkin's reagent contained in the lysing and Hb reagent. The reacted sample develops a color whose light absorption at 540 nanometers is proportional to Hb concentration.

When the sample is in the flow cell 75, it will absorb the light falling on the sample photodiode. The difference between the sample and reference photosensor outputs is then processed and measured in computer 84, and the test value displayed on the printer 112 and/or the CRT display 110.

Hematocrit determination is based upon the fact that the cell pulses generated by the electrodes during the RBC is proportional to cell volume. Further explanation of the process and the circuitry involved is provided in commonly assigned U.S. Pat. No. 3,812,425.

Using the measured RBC, Hct and Hb data, the microcomputer is programmed to calculate mean corpuscular volume, mean corpuscular hemoglobin, and mean corpuscular hemoglobin concentration according to the following formulas:

$$MCV (\mu^3) = \frac{Hct \times 10}{RBC \ (10^6 \ cells/mm^3)}$$

$$MCH (\mu\mu G) = \frac{Hb \ (G/DL) \times 10}{RBC \ (10^6 \ cells/mm^3)}$$

$$MCHC (\%) = \frac{Hb \ (G/DL) \times 100}{Hct \ (\%)}$$

These parameters are displayed on the CRT display or recorded by the printer.

In addition to allowing the Hb test to be conducted, the purge systems are useful in clearing debris and bubbles from the aperture.

Backflushing of the system can be accomplished by means of the three-way valve 88 and pump 58. Positive pressure is applied to the sump, and both heads may be flushed. Filters 22 and 42 are cleaned in this manner.

FIG. 3 illustrates a dual-type reservoir 200 which may be utilized in place of reservoirs 16 and 18. It comprises two container portions 202 and 204 which rest on a common base 206. Further support is obtained from connecting member 208. This feature provides the convenience of having to mount only one reservoir for supplying both heads with diluted blood samples.

It can be seen that the present invention provides a relatively inexpensive semi-automatic system for counting cells. The apparatus is approximately four times less expensive than currently available fully automated models, such as the Coulter S made by Coulter Electronics.

Because of the dual head feature, all components used for counting red or white blood cells can be optimized for the particular cell. Unlike conventional semi-automatic systems having only one head, no compromises are necessary to accommodate the different types of cell. Accordingly, the aperture sizes, flow rates, dilution ratios, filtering devices, and counting methods can all be optimized. Further advantages include the ability to obtain RBC and WBC simultaneously as to minimize the time of operation. The problems caused by cross-contamination, and in particular the lysing agent, are eliminated.

The tremendous cost saving of the invention over presently existing commercial units is also highly due to the fact that only one fluidics and analyzing circuit is necessary for each type of cell. Accurate data can be obtained by a means described in copending application entitled "Method and Apparatus For Providing Accurate Blood Cell Counts," Ser. No. 833,558 filed Sept. 15, 1977 and now abandoned. Multiple circuits and apertures are unnecessary for reliable performance, and a savings in material and cost is obtained. It is therefore possible to provide an apparatus which is applicable for both large institutional use, and use in smaller labs and doctors' offices. Present systems having the features of the invention are prohibitive in price for the latter two applications.

What is claimed is:

1. A semi-automatic instrument for analyzing prediluted blood samples, said instrument having at least two independent heads and associated circuitry for simultaneously determining red blood cell and white blood cell counts, comprising:
   a. a red blood cell counting (RBC) head having at least two electrodes therein, and an RBC aperture between at least two of the electrodes, means for receiving and releasably coupling with a first reservoir containing a first conductive liquid dilution having a blood sample with red blood cells and diluent in predetermined ratio for (RBC) counting;
   b. an RBC conduit for passing the first conductive liquid dilution containing red blood cells past the electrodes and through the RBC aperture, said RBC conduit extending into a reservoir containing the red blood cell dilution;
   c. means for applying an electrical signal through the aperture;
   d. RBC circuitry for producing pulses as cells suspended in the first dilution pass through the red blood cell aperture, said RBC circuitry being connected to electrodes located on opposite sides of the aperture;
   e. a white blood cell counting (WBC) head having at least two electrodes therein and a WBC aperture between at least two of said electrodes, means for receiving and releasably coupling a second reservoir containing a second conductive liquid dilution having the blood sample with white blood cells and diluent in a different predetermined ratio for (WBC) counting; f. a WBC conduit for passing the second conductive liquid dilution containing white blood cells past the electrode and through the WBC aperture, said WBC conduit extending into a reservoir containing the white blood cell dilution;
   g. means for applying an electrical signal through the WBC aperture;
   h. WBC circuitry for producing pulses as cell suspended in the second dilution pass through the WBC aperture, said WBC circuitry being connected to electrodes located on opposite sides of the aperture;
   i. means for detecting the pulses produced in both heads and for providing output indications corresponding to the number of particles pass through the apertures, respectively.

2. An instrument as described in claim 1 wherein the RBC aperture is about 70 microns in diameter.

3. An instrument as described in claim 1 wherein the WBC aperture is about 90 microns in diameter.

4. An instrument as described in claim 1 wherein means are provided for removing previous samples from the heads while flushing the aperture.

5. An instrument as described in claim 1 wherein a dual-type reservoir is employed for holding the WBC and RBC sample dilutions, respectively.

6. An instrument as described in claim 1 wherein platelets may also be counted in the RBC head.

7. An instrument as described in claim 1 wherein a hemoglobin head is in fluid communication with the WBC head.

8. An instrument as described in claim 1 wherein the sample fluids are aspirated through the heads due to the negative pressure applied by a pump.

9. An instrument as described in claim 1 wherein pneumatic filter means are provided for preventing pressure pulsations within the heads.

10. An instrument as described in claim 1 further comprising pulse amplitude discrimination means.

11. An instrument as described in claim 10 wherein dual threshold limits are provided to distinguish large and small pulses which are not representative of cells.

12. An instrument as described in claim 11 wherein means are provided for producing a real time display of the pulses as they occur, and the threshold limits which distinguish cell pulses from other pulses.

13. An instrument as described in claim 1 wherein the RBC head is coupled with a DC power source.

14. The invention in accordance with claim 13 wherein the RBC head comprises a set of three electrodes and the DC power source is connected across two of the electrodes.

15. The invention in accordance with claim 1 wherein an AC power source is connected with the WBC head.

16. The invention in accordance with claim 1 wherein each of the conduits includes a filter for filtering the conductive liquid dilutions before passing through the respective apertures.

* * * * *